United States Patent [19]
Harrison

[11] 3,937,805
[45] Feb. 10, 1976

[54] METHOD OF MAKING DENTIFRICE COMPOSITIONS CONTAINING INSOLUBILIZED SALTS OF 1,6-DI-(P-CHLOROPHENYL BIGUANIDO) HEXANE

[75] Inventor: Michael Harrison, Newcastle Upon Tyne, England

[73] Assignee: Colgate-Palmolive Company, New York, N.Y.

[22] Filed: Dec. 13, 1973

[21] Appl. No.: 424,388

Related U.S. Application Data

[63] Continuation-in-part of Ser. No. 197,498, Nov. 10, 1971, abandoned.

[52] U.S. Cl. ............... 424/52; 424/54; 260/404.5; 260/565
[51] Int. Cl.²... A61K 7/18; A61K 7/22; C09F 5/00; C07C 129/08

[58] Field of Search .............................. 424/49–58

[56] References Cited
UNITED STATES PATENTS
3,842,168   10/1974   Colodney............................ 424/54

*Primary Examiner*—Richard L. Huff
*Attorney, Agent, or Firm*—Robert L. Stone; Murray M. Grill; Herbert S. Sylvester

[57] ABSTRACT

Preparation of a dentifrice composition containing an insolubilized salt of 1,6-di-(p-chlorophenyl biguanido) hexane antimicrobial agent such as the disarcosinate monomeric salt or monofluorophosphate polymeric salt. The insolubilized salt may be pre-formed or formed in situ in the dentifrice composition. The insolubilized material is antimicrobially effective and provides desirable cosmetic effect.

15 Claims, No Drawings

METHOD OF MAKING DENTIFRICE COMPOSITIONS CONTAINING INSOLUBILIZED SALTS OF 1,6-DI-(P-CHLOROPHENYL BIGUANIDO) HEXANE

This application is a continuation-in-part of Ser. No. 197,498, filed Nov. 10, 1971, now abandoned.

This invention relates to dentifrice compositions which contain an antibacterial agent which is effective in promoting oral hygiene, such as by reducing dental plaque, improving gingival conditions and reducing formation of dental calculus. In particular, it relates to dentifrice compositions which contain such an agent in the form of a water-insoluble salt.

1,6-di-(p-chlorophenyl biguanido) hexane has been disclosed for its desirable effect in inhibiting the growth of many micro-organisms such as *Lactobacillus acidophilus odontolyticus* and has, therefore, been recommended for incorporation into oral compositions.

However, the use of this agent as the free base or in the form of water-soluble salts thereof such as the diacetate or digluconate has revealed some undesirable cosmetic effects such as brown dental enamel staining and bitter taste.

It is an object of this invention to prepare oral compositions which contain insolubilized 1,6-di-(p-chlorophenyl biguanido) hexane which do not stain teeth even upon repeated use and which do not impart an undesirable taste to the oral composition. Unexpectedly, these materials, although insoluble, are effective in promoting oral hygiene. Other advantages of the invention will be apparent from the following disclosure.

In accordance with certain of its aspects, this invention relates of preparing a dentifrice composition comprising a non-toxic insolubilized 1,6-di-(p-chlorophenyl biguanido) hexane antibacterial agent in amount corresponding to about 0.01–5% by weight of the free base thereof and a dentifrice vehicle in which said agent is distributed.

Water-insoluble salts of 1,6-di-(p-chlorophenyl biguanido) hexane include salts which are monomeric in nature and contain monovalent anions, such as the disarcosinate (particularly di-N-$C_{12}$-$C_{16}$ alkoyl sarcosinates), and dibenzoate salts, as well as salts which appear to be polymeric in nature and which contain polyvalent anions, such as salts of weak acids, including phosphate, citrates, malates, tartrates and tartronates, as well as fluorine containing salts, such as monofluorophosphates, hexafluoroaluminate, hexafluorosilicate, hexafluorostannate, fluorozirconate and the like.

These insoluble salts are typically formed by reaction between 1,6-di-(p-chlorophenyl biguanido) hexane or its relatively soluble salts such as the acetate, gluconate, fluoride and the like in aqueous solution with a salt or weak acid containing the desired anion to form a more insoluble salt. Since it is particularly desired to employ the insoluble salts in dentifrice compositions, it is preferable that the anion be acceptable and compatible with an oral composition such as a dentifrice or a mouthwash. Indeed, a soluble form of the antibacterial agent may react with an additional component of an oral composition such as sodium monofluorophosphate or sodium N-lauroyl sarcosinate to form the appropriate insoluble salt in situ. It is preferred that materials such as sodium carboxymethyl cellulose which form extremely insoluble salts with the antimicrobial agent not be present in oral composition, or if present, be in substantially less than stoichiometric amounts with regard to the antimicrobial agent.

The structure or formula apparently possessed by the insoluble monomeric salt and the polymeric salt may be as follows:

Monomer -
$Anion^-$ $^+Chlorhexidine^+$ $^-Anion$
wherein $^+Chlorhexidine^+$ refers to the cation of 1,6-di-(p-chlorophenyl biguanido) hexane and $Anion^-$ and $^-Anion$ each refer to a monovalent anion; and Polymer -
(...$^+Chlorhexidine$ $^+$$^-Anion$$^-$$^+Chlorhexidine^+$ ...)
wherein $^+Chlorhexidine^+$ has the meaning set forth above and $^-Anion^-$ is a polyvalent anion. In a polymer, typically at least 2 and even 10 or more Chlorhexidine moieties may be present. The compounds containing polyvalent anion described above constitute a particular aspect of this invention.

For dentifrice compositions, the disarcosinate monomeric salt and monofluorophosphate polymeric salts are particularly preferred; the former particularly because in the presence of up to stoichiometric amounts of N-lauroyl sarcosine or soluble salt thereof it forms a particularly antimicrobially effective precipitated salt and in the presence of excess N-lauroyl sarcosine or soluble salt thereof, it disperses in water and can, therefore, be easily incorporated into a mouthwash as well as a dentifrice, and the latter particularly because of its ability to provide fluorine to the composition. Furthermore, when the disarcosinate salt (e.g. the di-N-lauroyl sarcosinate salt) is formed and the amount of N-lauroyl sarcosine is less than up to stoichiometric with regard to the antimicrobial agent, particularly desirable control of the growth of antimicrobial organisms can be effected. This is especially the case when the precipitated salt is formed before incorporation into the dentifrice. It is preferred that such a preformed salt be dissolved in the flavour prior to incorporation into the dentifrice. The insoluble salts described in the instant specification may all be satisfactorily incorporated into oral and dentifrice compositions such as toothpastes or creams, or visually clear, i.e. transparent or translucent, dentifrice gels. Typically, they are present as discrete particles and in clear gels may actually be observed within or on the surface of the gel. Opaque creams may also be formulated to permit particles or stripes to be observed on the surface. Insoluble salts which can be dispersed, such as the disarcosinate salt in the presence of excess N-lauroyl sarcosine or water-soluble salt thereof, can be satisfactorily incorporated into a mouthwash as well as a dentifrice.

The insolubilized antibacterial agent is used in the oral composition in amount corresponding to 0.01–5% by weight, preferably 0.05–1%, based on the free base form of the antibacterial agent.

Dentifrice compositions which include the water-insoluble salt normally have a pH between about 5 and 10 and preferably about 6–8. The pH can be maintained with a buffering system. Citric acid, malic acid, tartaric acid and the like can be employed in such a buffering system. A portion of such materials can react in situ with 1,6-di-(p-chlorophenyl biguanido) hexane or water-soluble salt thereof to form the water-insoluble polymer. It is noted that at about pH 10, the free base of the antibacterial agent is insoluble and is, therefore, when in such state, included within the scope of the oral compositions of this invention. The dentifrice vehicle typically includes dentally acceptable substantially water-insoluble polishing agent of the type commonly employed in dental creams, chewable tablets, powders and visually clear gels. There is a relatively large number of such materials known in the art. Representative materials include, for example, dicalcium phosphate, tricalcium phosphate, insoluble sodium metaphosphate, aluminium hydroxide including hydrated alumina, colloidal silica, magnesium carbonate, calcium carbonate, calcium pyrophosphate, bentonite, etc., including suitable mixtures thereof. It is preferred to use the water-insoluble phosphate salts as the polishing agents and more particularly, insoluble sodium metaphosphate and/or a calcium phosphate, such as dicalcium phosphate dihydrate. Crystalline silica having particles of sizes up to about 5 microns, a mean particle size of up to about 1.1 microns, and a surface area of up to about 50,000 cm$^2$/g is also particularly desirable.

The hydrated alumina sold by Alcoa as C333, which contains 64.9% alumina, 0.008% silica, 0.003% ferric oxide, 0.25% sodium oxide, 0.37% moisture (at 10°C), all amounts being by weight, has a particle size such that all particles are less than 50 microns and 84% are less than 20 microns and has a specific gravity of 2.42, is a particularly desirable polishing agent in dentifrice compositions containing the insolubilized antibacterial agent, and particularly the insolubilized disarcosinate of 1,6-di-(p-chlorophenyl biguanido) hexane. When visually clear gels are employed, a polishing agent of colloidal silica, such as those sold under the trade mark Syloid as Syloid 72 and Syloid 74 or under the trade mark Santocel as Santocel 100 and alkali metal aluminosilicate complexes are particularly useful, since they have refractive indices close to the refractive indices of gelling agent-liquid (including water and/or humectant) systems commonly used in dentifrices.

The polishing agent may be the sole carrier material, particularly when the dentifrice is a tooth powder. Typically, other ingredients are present in the carrier and the amount of polishing agent is up to 95%, by weight of the carrier. In the case of a dental cream the polishing agent is generally about 20–75% by weight of the carrier, in a visually clear gel about 5–50% by weight and in a tooth powder or chewable tablet it is generally up to about 95% by weight of the carrier. When the aluminosilicate complex is employed it typically has a refractive index of about 1.44–1.47, up to about 20% by weight of moisture and up to about 10% by weight of sodium oxide.

In the preparation of tooth powders, it is usually sufficient to admix mechanically, e.g., by milling, the various solid ingredients, in appropriate quantities and particle sizes.

In dental cream and gel formulations the liquids and solids should necessarily be proportioned to form a creamy or gel mass of desired consistency which is extrudable from an aerosol container or a collapsible, e.g., aluminium or lead tube. In general, the liquid in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20 – 75% by weight of the formulation. In clear gels where the refractive index is an important consideration, about 10–30% by weight of water, 0 to about 80% by weight of glycerine and about 20–80% by weight of sorbitol is preferably employed. It is preferred to use also a gelling agent in dental creams and clear gels such as methyl cellulose, hydroxyethyl celluose, polyvinyl pyrrolidone and starch, usually in an amount up to about 10%, and preferably about 0.2-5% of the formula.

Organic surface-active agents which may be used in the compositions of the present invention to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material which imparts to the composition detersive and foaming properties. Suitably such detergents are water-soluble salts of substantially saturated higher aliphatic acyl amides of lower aliphatic amino carboxylic acid compounds, such as those having 12 to 16 carbons in the fatty acid, alkyl or acyl radicals, and the like.

Examples of the last mentioned amides are N-lauroyl sarcosine, and the sodium, potassium, and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Furthermore, the antibacterial agent and the sarcosinate can react in situ to form desirable insoluble salts in accordance with the invention.

Other particularly suitable surface active materials include nonionic agents such as condensates or sorbitan monostearate with approximately 60 moles of ethylene oxide, condensates of ethylene oxide with propylene oxide on propylene glycol ("Pluronics") and amphoteric agents such as quaternized imidazole derivatives which are available under the trademark "Miranol" such as Miranol C$_2$M.

It is noteworthy that insoluble salts including fluorine in the anion, such as the monofluorophosphate salt of 1,6-di-(p-chlorophenyl biguanido) hexane are particularly desirable in the presence of quaternized imidazole amphoteric surface active agents. Dentifrice compositions containing these materials are highly effective in preventing brown staining of dental enamel and possess substantially no bitter taste. These salts also effectively provide antibacterial effect to the dentifrice compositions. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethanoxy groups per molecule) and salts thereof with acids, and compounds of the structure

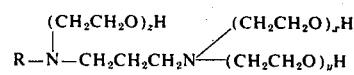

where R is a fatty alkyl group containing from about 12 to 18 carbon atoms, and x, y, and z total 3 or higher, as well as salts thereof with mineral or organic acids, may also be used. It is preferred to use from about 0.05 to 5% by weight of the foregoing surface-active materials in the instant oral preparations.

Various other materials may be incorporated in the oral preparations of this invention. Examples thereof are colouring or whitening agents or dyestuffs, preservatives, silicones, chlorophyll compounds, ammoniated materials such as urea, diammoniumphosphate and mixtures thereof, and other constituents. These adjuvants are incorporated in the instant compositions in amounts which do not substantially adversely affect the properties and characteristics desired and are selected and used in proper amount depending upon the particular type of preparation involved.

The insolubilized antibacterial agents employed in accordance with this invention do not impart a bitter or undesirable taste to oral compositions. The taste of the compositions may be modified by employing said suitable flavouring or sweetening materials. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and saccharine. Suitably, flavour-sweetening agent may together comprise from about 0.01 to 5% or more of the compositions of the instant invention.

The compositions of the present invention may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride ($SnF_2$-KF), potassium fluorozirconate, sodium hexafluorostannate, stannous chlorofluoride, and sodium monofluorophosphate. These materials, which dissociate or release fluorine-containing ions, suitably may be present in an effective but non-toxic amount, such as up to about 2% and usually within the range of about 0.1 to 1% by weight of the water soluble fluorine content thereof. Potassium hexafluorozirconate, sodium hexafluorostannate and sodium monofluorophosphate can form insoluble polymeric salts with the antibacterial agent in situ in the dentifrice composition and still be present in excess. Sodium fluoride, stannous fluoride and sodium monofluorophosphate are particularly preferred, as well as mixtures thereof.

Additional antibacterial agents may also be employed in the oral preparations of the instant invention to provide a total content of such agents of up to about 5% by weight. Typical antibacterial agents include $N^1$-(4-chlorobenzyl)-$N^5$-(2,4-dichlorobenzyl) biguanide;

p-chlorophenyl biguanido;

4-chlorobenzhydryl biguanide;

4-chlorobenzhydrylguanylurea;

N-3-lauroxypropyl-N5-p-Chlorobenhylbiguanide, 1-(lauryldimethylammonium)-8-(p-chlorobenzyl-dimethylammonium) octane dichloride;

5,6-dichloro-2-guanidoinobenzimidazole;

$N^1$-p-chlorophenyl-N5-laurylbiguanide;

5-amino-1,3-bis(2-ethylhexyl)-5-methylhexahydro pyrimidine;

1,6-bis-(2-ethylhexylbiguanido) hexane and their non-toxic acid addition salts.

Synthetic finely divided silica such as those sold under the trade marks Cab-o-Sil M-5, Syloid 244, Syloid 266 and Aerosil D-200 may also be employed in amounts of about 1–5% by weight to promote thickening or gelling and to improve clarity of the dentifrice.

When dentifrices, and particularly visually clear gels are prepared it may be desired to keep the gas or air content in the composition to a minimum. This may be particularly effectively done in the "Unimix" apparatus described in "Process Engineering", Sept. 11, 1970, Pages 81–85. In this apparatus a mixing tool can be rotated in clockwise or counter-clockwise manner, and the action of the mixing tool is followed by the action of a scraper blade to ensure that the working surface of the apparatus is scraped clean. Preferably, a plastic such as polytetrafluorethane is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid including water and/or humectant can be efficiently blended in the Unimix apparatus. Then the remaining liquid can be separately blended with the polishing agent and additional components (except for post-added components, such as flavouring oil) in the Unimix, and then the two dispersions blended together in the Unimix apparatus. If desired, the small amount of air can be largely removed under the depressurised conditions in the apparatus. The apparatus can be used to blend ingredients at room temperature as well as higher temperatures.

The following specific examples are further illustrative of the nature of the present invention but it is understood that the invention is not limited thereto. Oral compositions are prepared in the usual manner, except as indicated, and all amounts and proportions are by weight except as otherwise indicated.

EXAMPLE 1

The following dentifrice is prepared:

| The following Components | dentifrice is prepared: Parts |
|---|---|
| Glycerine | 20 |
| Hydroxyethylcellulose | 1.2 |
| Hydrated alumina (Alcoa C333) | 52 |
| Sodium N-lauroyl sarcosinate | 2 |
| 1,6-di-(p-chlorophenyl biguanido) hexane digluconate | 0.886 |
| Sodium saccharin | 0.2 |
| Flavour (peppermint) | 1 |
| Water | Balance to 100 |

In this dentifrice, 1,6-di-(p-chlorophenyl biguanido) hexane N-lauroyl disarcosinate is formed in situ and is dispersed due to the presence of excess sodium N-lauroyl sarcosinate.

The dentifrice above is also varied to include 0.125%, 0.25% and 0.5% of sodium N-lauroyl sarcosinate to form in situ precipitates of 1,6-di-(p-chlorophenyl biguanido) hexane di-N-lauroyl sarconsinates which provide effective control of bacterial growth, aids in reduction of formation of dental plaque, does not cause stain of dental enamel and is compatible with the flavour.

EXAMPLE 2

The following dentifrice is prepared:

| Components | Parts |
| --- | --- |
| Glycerine | 20 |
| Hydroxyethylcellulose | 1.2 |
| Crystalline Silica (Minusil 5 microns) | 45 |
| Miranol C$_2$M | 1 |
| 1,6-di-(p-chlorophenyl biguanido) hexane monofluorophosphate | 0.55 |
| Sodium saccharin | 0.2 |
| Flavour (spearmint) | 1 |
| Water | Balance to 100 |

In this dentifrice 1,6-di-(p-chlorophenyl biguanido) hexane monofluorophosphate is preformed and added together with the silica.

This dentifrice reduces the number of bacteria in the oral cavity, reduces formation of dental plaque, does not cause stain of dental enamel and has acceptable flavour.

EXAMPLE 3

The following dentifrice wherein precipitated 1,6-di-(p-chlorophenyl biguanido) hexane di-N-lauroyl sarcosinate is formed in situ is prepared:

| Components | Parts |
| --- | --- |
| Glycerine | 20 |
| Hydroxyethyl cellulose | 1 |
| Sodium saccharin | 0.2 |
| Hydrated alumina (Alcoa C333) | 52 |
| Miranol C$_2$M | 1 |
| Flavour | 1 |
| Ethanol | 0.5 |
| 1,6-di-(p-chlorophenyl biguanido) hexane digluconate (20% solution) | 4.428 |
| Sodium N-lauroyl sarcosinate | 0.607 |
| Water | 19.265 |

The dentifrice is prepared by dispersing hydroxyethyl cellulose in glycerine and separately dissolving sodium N-lauroyl sarcosinate in water. The solution is added to the dispersion together with sodium saccharin. 1,6-di-(p-chlorophenyl biguanido) hexane digluconate solution is then slowly added to the other components with mixing for 1–1½ hours. Hydrated alumina and then flavour and ethanol are then mixed into the preparation. Finally, Miranol C$_2$M is added and the dentifrice deaerated.

In the dentifrice British Aluminium MH 100 abrasive may replace Alcoa C333 as the hydrated alumina.

EXAMPLE 4

The following dentifrice containing preformed 1,6-di-(p-chlorophenyl biguanido) hexane di-N-lauroyl sarcosinate is prepared:

| Components | Parts |
| --- | --- |
| Glycerine | 20 |
| Hydroxyethyl cellulose | 1 |
| Sodium saccharin | 0.2 |
| Hydrated alumina (Alcoa C333) | 52 |
| Miranol C$_2$M | 1 |
| Flavour | 1 |
| Ethanol | 0.5 |
| 1,6-di-(p-chlorophenyl biguanido) hexane di-N-lauroyl sarcosinate | 1.06 |
| Water | 23.24 |

The dentifrice is prepared by rapidly stirring dispersing hydroxyethyl cellulose in glycerine. Sodium saccharin and water are added to the dispersion followed by hydrated alumina. Miranol C$_2$M and a solution of flavour, ethanol and 1,6-di-(p-chlorophenyl biguanido) hexane di-N-lauroyl sarcosinate are then mixed into the preparation. The dentifrice is then deaerated.

The dentifrice can also be prepared by adding solid 1,6-di-(p-chlorophenyl biguanido) hexane di-N-lauroyl sarcosinate together with the saccharin and water and mixing into the dispersion for 90 minutes.

The dentifrices of Examples 3 and 4 containing 1,6-di-(p-chlorophenyl biguanido) hexane di-N-lauroyl sarcosinate all aged well and exhibited antimicrobial activity. The greatest effectiveness against microorganisms was exhibited by the dentifrice in which the precipitate was preformed and dissolved in flavour during preparation.

EXAMPLE 5

1,6-di-(p-chlorophenyl biguanido) hexane monofluorophosphate is prepared by mixing dilute stoichiometric solutions of 1,6-di-(p-chlorophenyl biguanido) hexane digluconate and sodium monofluorophosphate in water to obtain an off-white oily precipitate of water-insoluble 1,6-di-(p-chlorophenyl biguanido) hexane monofluorophosphate, having a melting point of 183°–184°C.

EXAMPLE 6

1,6-di-(p-chlorophenyl biguanido) hexane citrate is prepared by mixing dilute solutions of sodium citrate and 1,6-di-(p-chlorophenyl biguanido) hexane digluconate. The product obtained 1,6-di-(p-chlorophenyl biguanido) hexane citrate, is first an oil at room temperature which slowly becomes a sticky solid.

It will be apparent to one skilled in the art that various modifications of the above Examples may be made thereto.

I claim:

1. A method of preparing a dentifrice composition which comprises mixing in a dentifrice vehicle a non-toxic insolubilized salt of 1,6-di-(p-chlorophenyl biguanido) hexane antimicrobial agent in amount corresponding to about 0.01–5% by weight of the free base thereof wherein said antimicrobial agent is in the form of a monomer salt selected from the group consisting of disarcosinate salt and dibenzoate salt and a polymer salt.

2. The method of preparing the dentifrice composition claimed in claim 1 wherein said insolubilized salt is preformed prior to mixing in said dentifrice vehicle.

3. The method of preparing the dentifrice composition claimed in claim 2 wherein said insolubilized salt is a polymer salt selected from the group consisting of phosphate, citrate, malate, tartrate, tartronate, monofluorophosphate, hexafluoroaluminate, hexafluorosilicate, hexafluorostannate and fluorozirconate.

4. The method of preparing the dentifrice composition claimed in claim 3 wherein said insolubilized salt is the monofluorophosphate salt.

5. The method of preparing the dentifrice composition claimed in claim 2 wherein said insolubilized salt is the di-N-lauroyl sarcosinate salt.

6. The method of preparing the dentifrice composition claimed in claim 5 wherein said insolubilized salt is formed by reaction of 1,6-di-(p-chlorophenyl biguanido) hexane or salt thereof with up to a stoichiometric amount of sodium N-lauroyl sarcosinate.

7. The method of preparing the dentifrice composition claimed in claim 6 wherein said preformed insolubilized salt is dissolved in flavour prior to incorporation into the dentifrice.

8. The method of preparing the dentifrice composition claimed in claim 1 wherein said insolubilized salt is formed in situ upon mixing in said dentifrice vehicle.

9. The method of preparing the dentifrice composition claimed in claim 8 wherein said insolubilized salt is the di-N-lauroyl sarcosinate monomer salt.

10. The method of preparing the dentifrice composition claimed in claim 8 wherein said insolubilized salt is a polymer salt selected from the group consisting of phosphate, citrate, malate, tartrate, tartronate, monofluorophosphate, hexafluoroaluminate, hexafluorosilicate, hexafluorostannate and fluorozirconate.

11. The method of preparing the dentifrice composition claimed in claim 10 wherein said insolubilized salt is the monofluorophosphate salt.

12. The method of preparing the dentifrice claimed in claim 1 wherein said dentifrice vehicle includes about 5–95% by weight of a dentally acceptable substantially water-insoluble polishing agent.

13. The method of preparing the dentifrice claimed in claim 12 wherein said dentifrice vehicle includes about 0.05–5% by weight of an amphoteric quaternized imidazole surface-active agent.

14. The method of preparing the dentifrice claimed in claim 12 wherein said dentifrice vehicle comprises a gelling agent and a liquid including water, a humectant or mixtures thereof.

15. The method of preparing the dentifrice claimed in claim 14 wherein said polishing agent is present in amount of about 20–75% by weight and comprises a hydrated alumina.

* * * * *